United States Patent
Suchan et al.

(10) Patent No.: US 8,020,728 B2
(45) Date of Patent: Sep. 20, 2011

(54) CONTAINER AND METHOD FOR OPENING A CONTAINER

(75) Inventors: Matthias Suchan, Hachenburg (DE); Alexander Bublewitz, Herborn (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 745 days.

(21) Appl. No.: 12/082,265

(22) Filed: Apr. 10, 2008

(65) Prior Publication Data

US 2008/0251535 A1    Oct. 16, 2008

(30) Foreign Application Priority Data

Apr. 16, 2007    (DE) .......................... 10 2007 018 143

(51) Int. Cl.
 *B67D 1/00*    (2006.01)
(52) U.S. Cl. ............................ 222/83; 220/277; 222/105
(58) Field of Classification Search ............. 222/80–91, 222/145.5, 145.6, 83.2, 105, 100; 220/583, 220/203.08, 277, 278; 215/297, 257; 383/200–202
See application file for complete search history.

(56) References Cited

U.S. PATENT DOCUMENTS

| | | | | |
|---|---|---|---|---|
| 3,608,782 A | * | 9/1971 | Sathicq | ............................ 222/94 |
| 4,461,454 A | * | 7/1984 | Vadnais | .......................... 251/350 |
| 6,352,177 B1 | * | 3/2002 | Bublewitz et al. | .............. 222/82 |
| 6,394,643 B1 | | 5/2002 | Bublewitz et al. | |
| 7,073,686 B2 | * | 7/2006 | Hanell | .......................... 222/83.5 |
| 2002/0113089 A1 | | 8/2002 | Nehren et al. | |
| 2005/0161454 A1 | | 7/2005 | Nehren et al. | |

FOREIGN PATENT DOCUMENTS

| | | |
|---|---|---|
| CH | 674 717 | 7/1990 |
| DE | 91 03 038 | 8/1992 |
| DE | 196 18 693 | 11/1997 |
| DE | 299 23 938 | 8/2001 |
| EP | 0 653 362 | 5/1995 |
| EP | 1 138 396 | 10/2001 |
| EP | 1 138 397 | 10/2001 |
| EP | 1 169 242 | 1/2002 |
| EP | 1 227 049 | 7/2002 |
| EP | 1 557 363 | 7/2005 |
| GB | 2 255 596 | 11/1992 |
| JP | 64-009128 | 1/1981 |
| JP | 8-502431 | 3/1996 |
| WO | WO 94/10119 | 5/1994 |

\* cited by examiner

*Primary Examiner* — Lien T Ngo
(74) *Attorney, Agent, or Firm* — Collard & Roe, P.C.

(57) ABSTRACT

A container for accommodating liquid and/or pasty substances is provided with a tubular outlet connector that is sealed via a film or a similar membrane relative to the substance accommodated in the container for storage. An inlet connector of a dispensing element can be inserted into the outlet connector. Furthermore, a piercing sleeve is displaceably accommodated in the outlet connector. The piercing sleeve can be displaced via setting on the inlet connector of the dispensing element so that the film or similar membrane is cut open. Furthermore, a combination of such a container and a dispensing element that can be connected with it, as well as a method for opening a container, are provided.

16 Claims, 3 Drawing Sheets

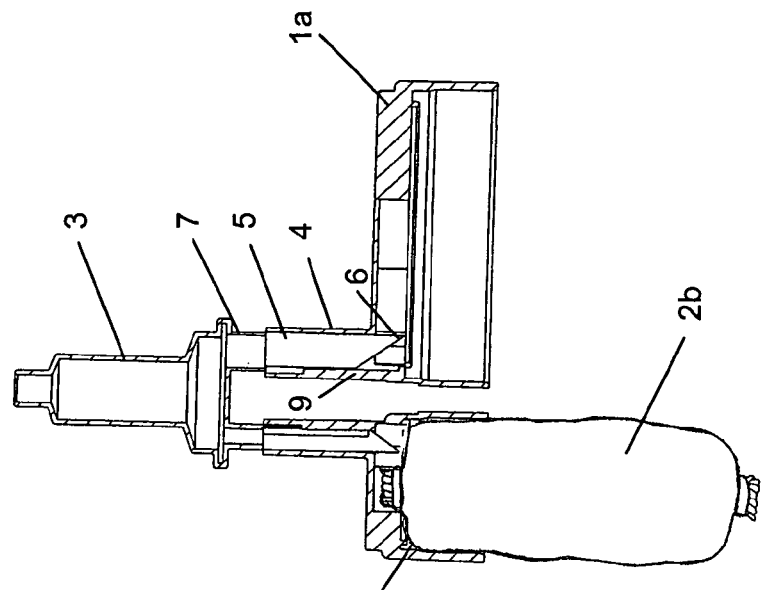
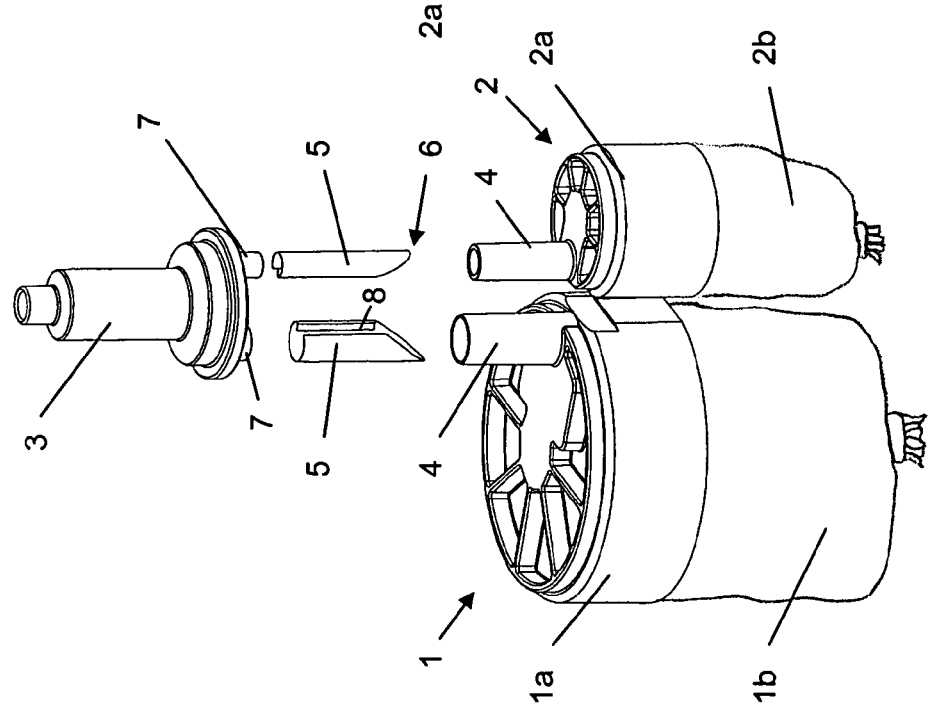

CONTAINER AND METHOD FOR OPENING A CONTAINER

CROSS REFERENCE TO RELATED APPLICATIONS

Applicants claim priority under 35 U.S.C. §119 of German Application No. 10 2007 018 143.6 filed Apr. 16, 2007.

BACKGROUND OF THE INVENTION

1. Field of the Invention

The present invention relates to a container for accommodating liquid and/or pasty substances. The container has a tubular outlet connector that is sealed via a film or a similar membrane, relative to the substance accommodated in the container, for storage, and is configured to accommodate an inlet connector of a dispensing element, which can be inserted into the outlet connector, in certain regions, and has a piercing sleeve that is displaceably accommodated in the outlet connector. Furthermore, the present invention relates to a combination of a container and a dispensing element, as well as to a method for opening a container.

2. The Prior Art

Liquid and/or pasty components are frequently offered in rigid, cartridge-like containers or in tubular bags that are connected with a rigid dispensing cap. To open such containers, it is necessary for a user to open up a film or the like before the first use, so that the substance accommodated in the container can exit. Because it is necessary to keep a suitable tool on hand for this purpose, this requirement is felt to be complicated and disadvantageous.

A device for opening a tubular bag containing a pasty substance is described in DE 299 23 938 U1, whereby an axially displaceable small piercing tube is provided in an accommodation cap connected with the tubular bag, in an outlet connector. This small tube can be manually displaced from a retracted position into an advanced position. In the retracted position, the small piercing tube does not project beyond the contact plane of the tubular bag, but projects out of the outlet connector on the opposite side. In the advanced position, the small piercing tube projects beyond the contact plane and thereby opens the tubular bag. In order to avoid unintentional opening of the tubular bag during transport and storage, a removable spacer is provided, by means of which the small piercing tube can be held in its retracted position. Similar devices are also known from EP 1 138 396 B1, EP 1 138 397 B1, EP 1 227 049 B1, and EP 1 557 363 A1. In the case of these devices, it can be felt to be a disadvantage that the spacer must be removed before opening the container, in some application cases. Furthermore, there is the risk of unintentional opening of the container if the spacer is not sufficiently secured.

Mixers are proposed in CH 674 717 A5 and DE 196 18 693 A1, which can be connected with containers as dispensing elements. In this connection, the inlet connectors of the mixers are configured as piercing taps that can pierce a tubular bag or the like to open it. Opening of the containers is therefore possible only using a mixer specially configured for this purpose.

Furthermore, tubular bags are described in DE 91 03 038 U1, in GB 2 255 596 A, and in EP 0 653 362 A1, in each instance, which can be pushed onto rigid piercing mandrels or the like by means of dispensing pistons. The mandrels are provided in a cap or cartridge. In this way, the tubular bags can be automatically opened by means of the advance movement or forward arching of the tubular bag during the emptying process. In this connection, however, there is the risk that the tubular bags already unintentionally make contact with the piercing mandrels during storage or transport, which could lead to opening of the tubular bags.

A film package is known from EP 1 169 242 B1, which consists of a tubular bag and a lid connected with the tubular bag, which lid can be connected with an outlet connector with a cap. A projecting mandrel for opening the tubular bag is provided in the cap. Furthermore, a blocking element is disposed in the outlet connector, which projects beyond the tip of the mandrel in the direction toward the tubular bag, so that unintentional opening of the tubular bag is prevented. To open the tubular bag, the blocking element is first removed from the outlet connector, and subsequently, the tubular bag is pushed further into the cap, with its lid, so that the mandrel penetrates into the tubular bag. To open a tubular bag, a user therefore has to perform multiple work steps.

SUMMARY OF THE INVENTION

It is therefore an object of the present invention to provide a container as well as a method for opening it, in which unintentional opening is avoided during transport or storage, and, at the same time, particularly simple opening of the container at its first use is made possible.

These and other objects are accomplished, according to the invention, substantially by providing a container of the type stated initially, in which the length of the outlet connector and of the piercing sleeve are coordinated with one another so that the piercing sleeve can be displaced from a storage position, into an activation position by means of inserting the inlet connector of the dispensing element into the outlet connector.

In the storage position, the piercing sleeve does not project out of the outlet connector. In the activation position, the piercing sleeve penetrates and/or at least approximately touches the film. Because the piercing sleeve preferably does not come into contact with the film in its storage position, there is no risk that the container will be unintentionally opened during transport or storage, if the film is damaged. In contrast, the container can be easily opened if a mixer or a similar dispensing element is set onto the container. This setting on of the mixer is generally carried out intuitively by most users, so that the container is opened without any additional work step, by setting on the mixer or similar dispensing element.

This arrangement furthermore has the advantage that the container remains sealed until immediately before its first use. Unintentional exit of the substances contained in the container and/or penetration of germs or contaminants into the container is effectively prevented in this manner. An airtight package until immediately before the first use is also decisive for storage stability in the case of many products used in the dental sector. For secure opening, it is preferred if the piercing sleeve penetrates the film. It can also be sufficient, however, to displace the piercing sleeve only so far that it touches the film or at least is positioned very close to the film. In this way, the film is opened only during forward arching when emptying pressure is applied.

According to a preferred embodiment of the invention, the container is formed by a tubular bag and a rigid cap connected with the tubular bag, on which cap the outlet connector is provided. In this connection, the tubular bag forms the film or similar membrane that seals the outlet connector. Such tubular bags have the advantage that the container, which is frequently a disposable article, has a comparatively low weight and can be disposed of in space-saving manner.

Alternatively, the container can also be configured as a rigid cartridge, on the face of which the outlet connector is provided. In this connection, the outlet connector can be sealed for storage via a film or similar membrane. For example, the film or membrane may seal the outlet connector in the plane of the face of the cartridge, i.e. for example at the cartridge-side end of the outlet connector.

If the piercing sleeve is formed from an elastic material, particularly spring steel, as a sleeve slit in the longitudinal direction, the piercing sleeve can be held within the outlet connector, essentially so as not to come loose. For this purpose, the piercing sleeve is introduced into the outlet connector under bias, if necessary, so that the piercing sleeve rests closely against the inside wall of the outlet connector. Unintentional opening of the container via displacement of the piercing sleeve, for example due to severe shocks during transport, can be avoided in this manner. It must be taken into consideration in the selection of a suitable material for the piercing sleeve, however, that the piercing sleeve must be sufficiently rigid to be able to open a tubular bag or similar film. Alternatively or in addition to wedging the piercing sleeve in the outlet connector under bias, spreading spring arms and/or counter-hooks can also be provided, for example, which prevent the piercing sleeve from being pulled out, according to the principle of a dowel. This arrangement is particularly important if material is supposed to be dispensed without a mixer being set on, for example in the case of a function check.

In a further embodiment, the piercing sleeve has means for fixing the piercing sleeve in place in the outlet connector, particularly in releasable manner. Thus, the piercing sleeve can be locked in place in the outlet connector in its storage position and/or in its activation position, for example. Furthermore, a locking device, for example a hook or a stop, can also be provided, in order to limit the displacement path of the piercing sleeve in the outlet connector.

In order to allow fast and reliable opening of the container, the piercing sleeve preferably has at least one tip formed by a slanted part, for example, and/or one cutting edge, on its side facing the film. In this connection, opening of the container can take place in that the piercing sleeve cuts into the film or cuts out a region of the film, or that the film is weakened or caused to burst. Where the piercing sleeve cuts out a region of the film, the cut-out region of the film preferably still remains connected with the remaining film. In this way, the mixer or similar dispensing element is not plugged up by a punched-out piece of film.

Specifically when the piercing sleeve is made from spring steel, the piercing sleeve can be produced from a comparatively thin sheet-metal strip. To ensure that the piercing sleeve can be displaced within the outlet connector by the mixer or similar dispensing element, the piercing sleeve advantageously has a projection that projects radially inward, at least on its side facing away from the film. This projection serves as an additional contact surface for the inlet connector of the dispensing element that can be inserted into the outlet connector, by means of which displacement of the piercing sleeve is brought about. If the piercing sleeve is configured as a slit sleeve, at least one of the edges of the piercing sleeve that run in the axial direction, along the slit, can be bent inward to form such a projection. This embodiment has the advantage, as compared with a beaded edging or the like, that the lumen is only marginally reduced in size.

In some application cases, it is desirable if the tip of the piercing sleeve impacts the film at a defined location, in order to open it. For this purpose, the piercing sleeve and the outlet connector can have means for aligning and/or preventing rotation of the piercing sleeve in the outlet connector, which means are assigned to one another. This arrangement can be achieved, according to one embodiment of the invention, in that the outlet connector has a cross-section that does not have rotation symmetry, at least in certain regions, and the piercing sleeve is adapted to this geometry. Alternatively or in addition, a crosspiece or similar projection can be provided on the inside of the outlet connector, the width of which is coordinated with that of the slit of the piercing sleeve, so that the piercing sleeve is guided in the outlet connector.

In another aspect, the invention furthermore relates to a combination of at least one container for accommodating liquid and/or pasty substances and a dispensing element that can be connected with it. The container has a tubular outlet connector that can be sealed by a film or similar membrane, in which connector a piercing sleeve is displaceably accommodated. The dispensing element has at least one inlet connector that can be inserted into the outlet connector, in each instance. In this connection, the length of the outlet connector, of the inlet connector, and of the piercing sleeve are coordinated with one another so that the piercing sleeve can be displaced from a storage position, in which the piercing sleeve does not project out of the outlet connector, into an activation position, in which the piercing sleeve penetrates and/or touches the film, via inserting the inlet connector of the dispensing element into the outlet connector.

In this connection, the dispensing element can be a mixer whose inlet connectors can be inserted into the outlet connectors of two containers. Particularly when using this combination, according to the invention, in the dental sector, two containers are preferably combined to form a double cartridge. This arrangement can be done, for example, by rigidly connecting cartridge-like containers with one another, or by providing a connection element in order to connect two tubular bag packages with one another. The mixer can be both a dynamic, i.e. driven mixer, and a static mixer. It is also possible, however, to provide other dispensing elements, for example an applicator, which can be set onto a container with an inlet connector, so that the piercing sleeve is displaced to open the container.

In the method according to the invention for opening a container, the tubular outlet connector of the container is sealed by a film or similar membrane, at first, whereby a piercing sleeve is displaceably accommodated in the outlet connector. To open the container, an inlet connector of a dispensing element is inserted into the outlet connector so that as a result, the piercing sleeve is displaced from a storage position into an activation position. In the storage position, the piercing sleeve does not project out of the outlet connector, and preferably also does not stand in contact with the film. In contrast, in its activation position, the piercing sleeve is displaced so far toward the film that the film is at least weakened via the contact with the piercing sleeve, and then bursts or tears open when an emptying pressure is applied to the container. Preferably, however, the piercing sleeve pierces or cuts through the film. It can also be sufficient, however, to displace the piercing sleeve only so far that it is at least positioned very close to the film, so that the film is opened only when it arches forward, when an emptying pressure is applied.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention. In this connection, all of the characteristics described and/or shown in the drawings represent embodiments of the invention, in themselves or in any desired combination, independent of how they are combined in the claims or their antecedents.

In the drawings, wherein similar reference characters denote similar elements throughout the several views:

FIG. 1 is a perspective view of two containers with separate piercing sleeves and a mixer;

FIG. 2 shows a section through two containers before the mixer is set on;

FIG. 3 shows two containers with the mixer set on;

DETAILED DESCRIPTION OF PREFERRED EMBODIMENTS

Figure 4:
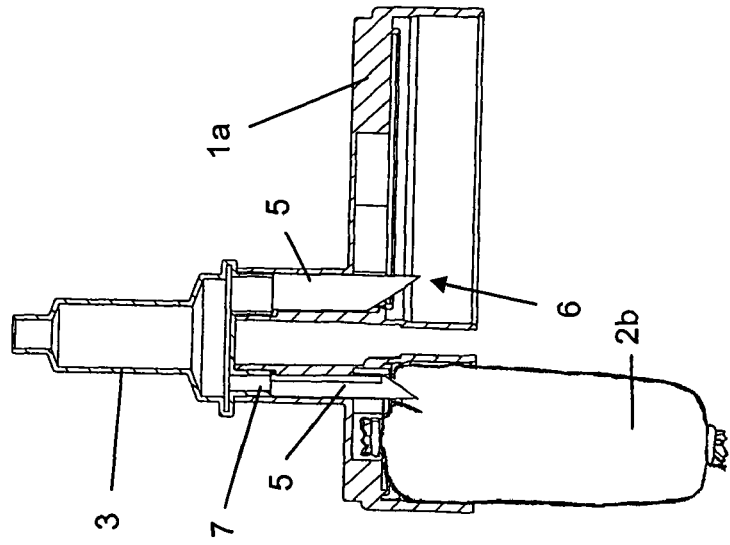
FIG. 4 shows a section through the container according to FIG. 3.

Referring now in detail to the drawings, in the exemplary embodiment shown in FIGS. 1 to 4, two containers 1 and 2 assigned to one another are provided, onto which a common mixer 3 can be set. In this connection, the containers are essentially formed by rigid caps 1a, 2a as well as tubular bags 1b, 2b connected with them. Tubular bags 1b, 2b that are made up of a flexible film material or a similar membrane can be glued into caps 1a, 2a, for example, or connected with them in some other way, preferably forming a seal.

Each of the two caps 1a, 2a has a tubular outlet connector 4, which projects from the face of the caps. As can be seen in the sectional view of FIGS. 2 and 4, in which only one tubular bag 2b is shown, in each instance, for reasons of a clearer illustration, the tubular bags make contact, at least in certain regions, with a face-side stop wall or delimitation wall of caps 1a and 2a. A piercing sleeve 5 can be inserted into outlet connectors 4, in each instance. Piercing sleeves 5 can be made up of spring steel, for example, or another sufficiently rigid and elastic material. On their side facing the tubular bags 1b, 2b, a tip 6 or a cutting edge with which the film material of the tubular bags can be cut is formed on each piercing sleeve 5, by means of a slanted part.

Mixer 3, indicated only schematically in the drawings, has two inlet connectors 7, whose outside diameter is adapted to the inside diameter of outlet connectors 4, in such a manner that inlet connectors 7 can be inserted into outlet connectors 4, essentially forming a seal.

Figure 5:
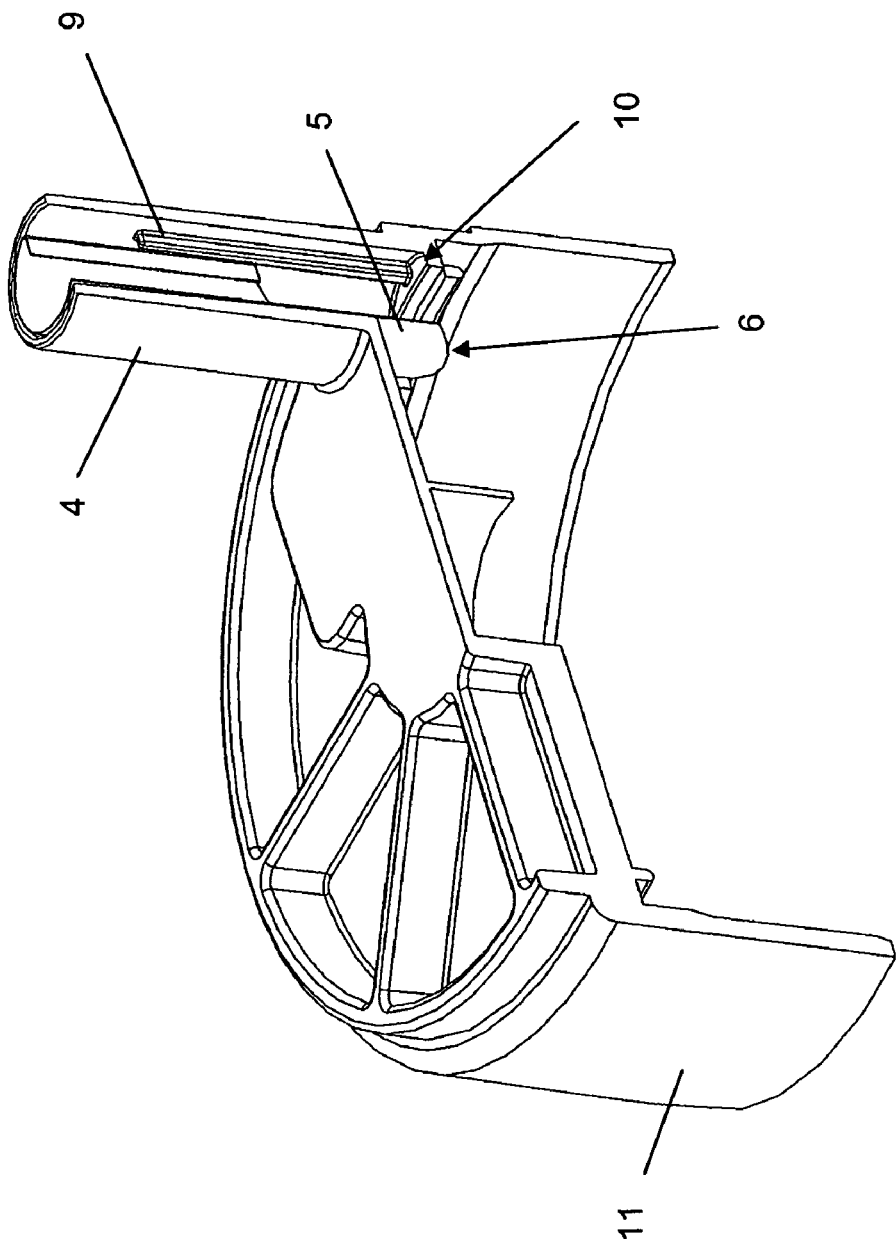
FIG. 5 is an enlarged representation of a broken-open cap with a piercing sleeve inserted.

As can be seen in the representation of FIGS. 2 and 5, the length of outlet connectors 4 and the length of piercing sleeves 5 are adapted to one another in such a manner that piercing sleeves 5 can be introduced into outlet connectors 4 in such a manner that piercing sleeves 5 neither project out of the end of outlet connectors 4 that faces mixer 3, nor project beyond the face-side stop surface of caps 1a, 2a. In this storage position, shown in FIGS. 2 and 5, tips 6 of piercing sleeves 5 therefore do not come into contact with the tubular bags. Because piercing sleeves 5 are completely accommodated in outlet connectors 4, there is also no danger that piercing sleeves 5 are unintentionally displaced further in the direction toward the tubular bags.

Figure 3:
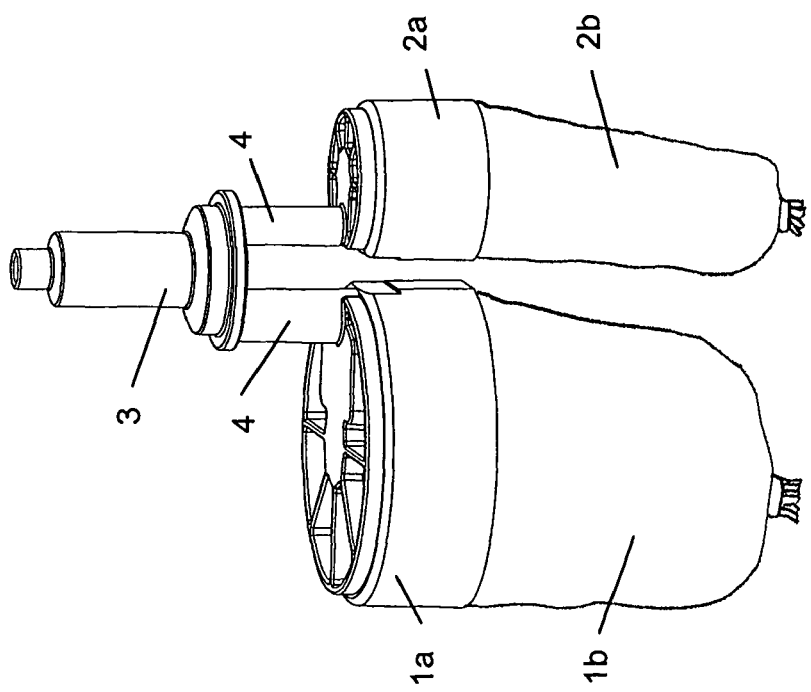

As shown in FIG. 3, mixer 3 can be set onto containers 1 and 2, so that inlet connectors 7 of mixer 3 penetrate into outlet connectors 4 of caps 1a and 2a. In this way, piercing sleeves 5 accommodated in outlet connectors 4 are displaced into the activation position shown in FIG. 4, i.e. in the direction toward tubular bags 1b, 2b. In this connection, tips 6 of piercing sleeves 5 cut the material of tubular bags 1b, 2b, so that substances accommodated in containers 1 and 2, respectively, can flow through piercing sleeves 5 and outlet connectors 4, into mixer 3, by way of inlet connectors 7. Containers 1 and 2 can consequently be opened by setting on mixer 3, and the axial displacement of piercing sleeves 5 that results therefrom.

Piercing sleeves 5 can be bent from a sheet-metal part, in particularly simple manner, and therefore have a longitudinal slit 8. As shown in FIGS. 1 and 5, an axial longitudinal edge of piercing sleeve 5 that is adjacent to slit 8 is bent inward. As a result, a larger contact surface between piercing sleeve 5 and inlet connectors 7 of mixer 3 occurs. Inlet connectors 7 of mixer 3 can therefore not be inserted into the piercing sleeves 5 even if particularly thin sheet metals are used. Alternatively, a beaded edge can also be provided on piercing sleeve 5, which enters into contact with the inlet connectors of the mixer.

At the same time, the region of piercing sleeve 5 that is bent inward, together with slit 8, serves to guide piercing sleeve 5 in outlet connector 4. For this purpose, a crosspiece 9 that projects radially inward is provided in outlet connector 4; crosspiece 9 has a width that approximately corresponds to the width of slit 8 of piercing sleeve 5. In this manner, piercing sleeves 5 are guided in outlet connectors 4 so that they cannot rotate. This feature is important so that tips 6 are positioned at a location at which optimal opening is made possible. Thus it is preferred if tips 6 do not come into contact with pleats of tubular bags 1b, 2b, if at all possible.

On the side of crosspiece 9 that faces the tubular bags, a stop surface 10 is formed, which limits the movement of piercing sleeve 5 in the direction toward the tubular bags. In the opposite direction of movement, piercing sleeves 5 are held in the outlet connectors 4 via their elastic bias. In this way, piercing sleeves 5 cannot fall out of outlet connectors 4 during transport.

Alternatively to the embodiment of the containers shown in FIGS. 1 to 5, essentially rigid, cartridge-like containers can also be provided according to the invention. For this purpose, the cylindrical wall 11 of the caps that projects downward in FIG. 5 can be lengthened accordingly, for example. The substances to be stored can then be filled directly into the container formed in this manner. To close outlet connectors 4, a film or similar membrane can be provided, for example in the plane of the face-side stop surface of the caps, to prevent the substances from running out. This film or membrane can be cut as described above, via setting on a mixer and thereby displacing piercing sleeves 5.

According to another embodiment of the invention, not shown in the drawings, the mandrel sleeve can project outward out of the connector in its storage position. In this connection, the inlet connectors of the mixer do not penetrate into the outlet connectors, but rather engage around them when the mixer is connected with the containers. The inlet connectors of the mixer are provided with an inner projection, a step, or another suitable stop surface, which enters into contact with the mandrel sleeve, in each instance, when the mixer is set onto the containers. In this way, the mandrel sleeve is activated, i.e. displaced in the direction toward the film, so that the film is opened either directly or by means of applying an emptying pressure.

Furthermore, it is also possible, according to the invention, to provide a combination of the two embodiments described above, in the case of two containers that can be connected with a mixer, so that one inlet connector of the mixer penetrates into an outlet connector, while the other inlet connector of the mixer engages around an outlet connector.

Although only a few embodiments of the present invention have been shown and described, it is to be understood that many changes and modifications may be made thereunto without departing from the spirit and scope of the invention as defined in the appended claims.

What is being claimed is:

1. A container for accommodating a liquid or pasty substance comprising:
   (a) a tubular outlet connector of the container having an outlet connector length;
   (b) a storage container comprising a membrane sealing the outlet connector relative to the substance accommodated in the storage container;
   (c) a dispensing element comprising an inlet connector, said inlet connector being insertable into the outlet connector in certain regions; and
   (d) a piercing sleeve displaceably accommodated in the outlet connector under bias, said piercing sleeve having a piercing sleeve length;
   wherein said outlet connector length and said piercing sleeve length are coordinated with another so that the piercing sleeve is displaceable from a storage position, wherein the piercing sleeve does not project out of the outlet connector, into an activation position, wherein the piercing sleeve penetrates or at least approximately touches the membrane via inserting the inlet connector into the outlet connector.

2. The container according to claim 1, wherein the storage container comprises a tubular bag and a rigid cap connected with the tubular bag, the outlet connector being provided on said cap, the tubular bag forming the membrane that seals the outlet connector.

3. The container according to claim 1, comprising a rigid cartridge having a face, wherein the outlet connector is provided on said face, the outlet connector being sealable for storage via the membrane at a cartridge-side end of the outlet connector.

4. The container according to claim 1, wherein the piercing sleeve is formed from an elastic material as a sleeve slit in the longitudinal direction.

5. The container according to claim 4, wherein the piercing sleeve is formed from spring steel.

6. The container according to claim 1, wherein the piercing sleeve has a fixing element fixing the piercing sleeve fixing in place in the outlet connector in a releasable manner or limiting a displacement path of the piercing sleeve.

7. The container according to claim 1, wherein the piercing sleeve has at least one tip formed by a slanted part, or at least one cutting edge on a side of the piercing sleeve facing the storage container.

8. The container according to claim 1, wherein the piercing sleeve has a projection that projects radially inward, at least on a side of the piercing sleeve facing away from the storage container.

9. The container according to claim 1, wherein the piercing sleeve and the outlet connector have a mechanism for aligning or preventing rotation of the piercing sleeve in the outlet connector.

10. A combination comprising:
    (a) at least one container for accommodating a liquid or pasty substance; and
    (b) a dispensing element connectable with said at least one container;
    wherein said at least one container comprises a tubular outlet connector of the container having an outlet connector length, a storage container comprising a membrane and a piercing sleeve displaceably accommodated in the outlet connector under bias and having a piercing sleeve length;
    wherein said dispensing element comprises at least one inlet connector having an inlet connector length, said inlet connector being insertable into the outlet connector; and
    wherein said outlet connector length, said inlet connector length, and said piercing sleeve length are coordinated with one another so that the piercing sleeve is displaceable from a storage position, wherein the piercing sleeve does not project out of the outlet connector, into an activation position, wherein the piercing sleeve touches or penetrates the membrane via inserting the inlet connector into the outlet connector.

11. The combination according to claim 10, wherein the storage container comprises a tubular bag and a rigid cap connected with the tubular bag, the outlet connector being provided on said cap, the tubular bag forming the membrane that seals the outer connector.

12. The combination according to claim 10, comprising first and second containers, wherein the dispensing element is a mixer comprising first and second inlet connectors insertable into the respective outlet connectors of the containers.

13. A method for opening a container comprising the steps of:
    (a) providing a container comprising a tubular outlet connector of the container sealed by a membrane and a piercing sleeve displaceably accommodated in the outlet connector under bias; and
    (b) inserting an inlet connector of a dispensing element into the outlet connector so that the piercing sleeve is displaced from a storage position, wherein the piercing sleeve does not project out of the outlet connector, into an activation position, wherein the piercing sleeve touches or penetrates the membrane.

14. The method for opening a container according to claim 13, wherein the piercing sleeve is formed from elastic spring steel.

15. The method for opening a container according to one of claim 13, wherein the piercing sleeve is slit or provided with a beaded edge.

16. The method for opening a container according to claim 13, wherein the piercing sleeve is secured in the outlet connector via a rotation prevention device.

* * * * *